(12) United States Patent  (10) Patent No.: US 8,175,699 B2
Szeles  (45) Date of Patent: May 8, 2012

(54) PUNCTUAL STIMULATION APPARATUS

(76) Inventor: Jozsef Constantin Szeles, Vienna (AT)

( * ) Notice: Subject to any disclaimer, the term of this patent is extended or adjusted under 35 U.S.C. 154(b) by 261 days.

(21) Appl. No.: 12/450,931

(22) PCT Filed: Apr. 21, 2008

(86) PCT No.: PCT/AT2008/000144
§ 371 (c)(1),
(2), (4) Date: Oct. 19, 2009

(87) PCT Pub. No.: WO2008/128270
PCT Pub. Date: Oct. 30, 2008

(65) Prior Publication Data
US 2010/0168822 A1 Jul. 1, 2010

(30) Foreign Application Priority Data
Apr. 20, 2007 (AT) ................................ GM253/2007

(51) Int. Cl.
A61N 1/00 (2006.01)
(52) U.S. Cl. .......................................................... 607/2
(58) Field of Classification Search .................. 607/2, 3, 607/17, 45, 120
See application file for complete search history.

(56) References Cited

U.S. PATENT DOCUMENTS

| 4,267,838 A | 5/1981 | McCall |
| 5,025,807 A | 6/1991 | Zabara |
| 5,397,338 A | 3/1995 | Grey et al. |
| 7,336,993 B1 | 2/2008 | Szeles |
| 2007/0203532 A1* | 8/2007 | Tass et al. ........................ 607/45 |
| 2007/0250145 A1 | 10/2007 | Kraus et al. |
| 2010/0262205 A1* | 10/2010 | De Ridder ....................... 607/17 |
| 2010/0331807 A1* | 12/2010 | Whitehurst et al. ........... 604/500 |

FOREIGN PATENT DOCUMENTS

| AT | 407 343 | 2/2001 |
| AT | 004 325 | 6/2001 |
| DE | 295 17 993 | 1/1996 |
| DE | 10 2005 003 7 | 7/2006 |
| EP | 0 160 753 | 11/1985 |
| EP | 0 323 052 | 7/1989 |
| WO | WO 98/05379 | 2/1998 |
| WO | WO 01/35897 | 5/2001 |

OTHER PUBLICATIONS

International Search Report.
Sator-Katzenschlager, S. M. et al., "The Short- and Long-Term Benefit in Chronic Lower Back Pain Through Adjuvant Electrical Versus Manual Auricular Acupuncture," Anesthesia & Analgesia, vol. 98, 2004, pp. 1359-1364, XP-002488596. (ISR).

* cited by examiner

Primary Examiner — George Manual
Assistant Examiner — Robert Wieland
(74) Attorney, Agent, or Firm — Collard & Roe, P.C.

(57) ABSTRACT

An apparatus is disclosed for punctually stimulating nerve endings located in the region of the ears, said nerve endings extending to brain stem nuclei. The apparatus (1) has a support (2) which is to be positioned in the region of the neck or the upper arm of a patient, and which is provided with at least some of the electrically active structural components (4, 7, 13) of the apparatus (1) arranged for forming a therapeutic current, and which furthermore accommodates feed batteries (3) that deliver at least part of the operating power for the apparatus.

9 Claims, 5 Drawing Sheets

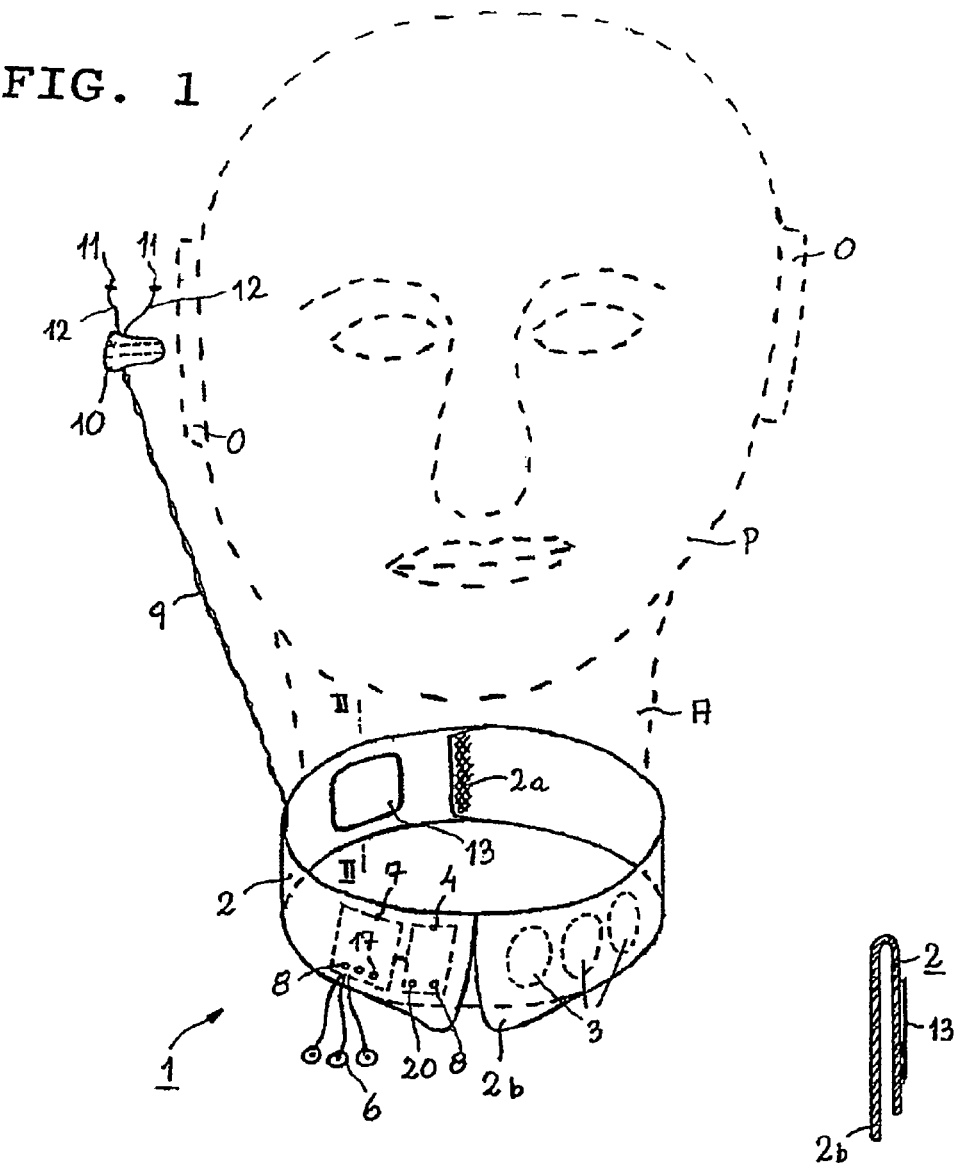

PUNCTUAL STIMULATION APPARATUS

CROSS REFERENCE TO RELATED APPLICATIONS

This application is the National Stage of PCT/AT2008/000144 filed on Apr. 21, 2008, which claims priority under 35 U.S.C. §119 of Austrian Application No. GM 253/2007 filed on Apr. 20, 2007. The international application under PCT article 21(2) was not published in English.

The invention relates to an apparatus for punctually stimulating nerve endings located in the region of the ears, said nerve endings extending to the brain stem nuclei, said apparatus comprising a battery-fed therapeutic-current generator, the latter being provided with an electronic circuit that forms low-frequency therapeutic current, and said apparatus further comprising at least one electrode that is to be positioned at an nerve ending, and that is connected to the therapeutic-current generator via a separate flexible line.

It is an object of the invention to create an apparatus of the above-mentioned type which exhibits improved properties as regards therapeutic application. It shall be possible to undergo the stimulation therapy over several days without breaks and without substantially interfering with the living conditions, and to optionally do one's job, yet handling of the apparatus shall be simple, the stimulation current shall be largely independent from outer influences and, moreover, it shall be rendered possible to use the apparatus in a wide range of application fields.

According to a first aspect of the invention, it is provided that a current-constancy circuit arrangement is arranged in the therapeutic-current generator that stabilizes the therapeutic current against resistor changes in the electrode-patient electric circuit.

In this manner, it is possible to largely eliminate the influence of external factors, e.g. possible changes in the electrical resistor in the therapeutic-current circuit, in particular in the region of the skin, on the stimulation-current values to be reached during therapy.

According to a second aspect of the invention, it is provided that the apparatus has a support to be arranged in the region of the neck or the upper arm of a patient, said support accommodating feed batteries that deliver at least part of the operating power of the apparatus, and said support further having at least some of electrically-active structural components of the apparatus arranged for forming the therapeutic current.

In this context, it is preferably provided for the support to be configured in the form of a collar or tape to be laid around the neck or the upper arm of a patient.

The advantage of providing a support which is to be positioned in the region of a patient's neck or upper arm and which accommodates batteries for feeding the apparatus and at least some of the electrical structural components serving for forming the therapeutic current, is that these elements of the apparatus are positioned in the vicinity of the region of the ears, on the one hand, and well accessible, on the other hand, what is beneficial for exchanging batteries and for control measures and adjustment manipulations of the therapeutic current, e.g. It is easily possible to provide for a stable fixing on the body and to optionally cover the support with clothing. When exchanging batteries and manipulating the support-borne electrical structural components, e.g. when adjusting or changing a therapeutic-current program, it is possible to avoid negative mechanical influence of the electrode positioned in the region of the ears. The above-mentioned preferred configuration of the support in the form of a collar or a tape allows for a particularly good fit of the support on the body. Such a collar can optionally have the form of a neck cuff, i.e. have a flexible overlap.

In addition to structural components that are provided directly in the electric circuit of the therapeutic current, e.g. base electrode or a semiconductor element directly connected to an ear-region-positioned electrode, the electrically-active structural components that are arranged for therapeutic-current formation also comprise controlling switching circuits of the electronic circuit that forms the therapeutic current. If the support is provided with a base electrode, the base electrode can be arranged on a short flexible line on the support so that the contact point at which said base electrode contacts the skin can be chosen; it is also possible to arrange a base electrode that is configured in the form of a plate electrode on that side of the support that is to be contacted with the surface of the patient's skin, wherein both a good fit of the support and a stable pressure of the base electrode against the patient's skin are ensured. Likewise, also at least one therapeutic-current generator, which comprises a therapeutic-current-forming electronic circuit and feeds this current to a stimulating nerve ending via at least one electrode, can be provided on the support as a whole, i.e. fixedly connected with the support and/or integrated therewith, or detachably fixed on the same, with latter configuration offering advantages as regards manufacture and also long-term therapy with possible changes of stimulation over time. Yet, also at least one therapeutic-current generator can be located in the region of the ears and connected to electrically-active support-borne structural components via flexible lines. Such lines can form, e.g., a connection to a support-borne base electrode or a connection to support-borne feed batteries or a connection to switching circuits that controllably influence an electronic circuit provided in the therapeutic-current generator. Such switching circuits can be arranged on the support to be well accessible so as to allow for adjustments or adjusting settings that are to influence the therapeutic current, and for monitoring of the signals flowing in said switching circuits by means of equipment to be connected, and for delivering of external signals that may originate from body-function sensors, in a trouble-free manner. If only control signals need to be transmitted from support-borne switching circuits to an electronic circuit of an ear-region-arranged therapeutic-current generator, a wireless connection, i.e. a transmitter-receiver track, can also be advantageously provided as a connection.

Body-function sensors, e.g. sensors for cardiac-action potentials, sensors for pulse, or sensors for brain waves, can be connected to the support-borne switching circuits in a mechanically and electrically stable manner, said switching circuits including a circuit that generates control signals from the output signals of such sensors.

The inventively configured apparatus allows for different body functions, e.g. pulse rate and blood pressure, to be influenced in a virtually non-invasive manner by stimulating nerve endings located in the region of the ears, wherein a controlled stimulation may result in a specific change in the body-function parameters, in particular to achieve normalization. This influencing preferably occurs based on signals derived from body functions whose parameters are to be changed. An embodiment of the apparatus preferred in this respect is characterized in that the apparatus, preferably the support, is provided with at least one sensor for body functions of a patient, said sensor emitting electrical output signals, that the apparatus, preferably the support, furthermore comprises electronic switching circuits that form control signals from the output signal of the body-function sensor, said control signals being provided for body-function-dependent control of at least one therapeutic-current generator, and that an electrical signal connection is furthermore provided that extends to at least one therapeutic-current generator for influencing the therapeutic current via the control signals derived from the output signals of the sensor.

An advantageous further configuration of this embodiment is characterized in that the electronic switching circuits, which form control signals for the therapeutic-current generator from the output signal of the body-function sensor, comprise a time-delay stage that can be triggered by the periodic output signal of a body-function sensor and whose delay time is adjustable, the time-delay stage itself activating the therapeutic-current generator that delivers a periodic therapeutic current to at least one electrode to be arranged at a nerve ending located in the region of a patient's external ear, with the repetition rate of the therapeutic current corresponding to the repetition rate of the output signal of the body-function sensor, with the therapeutic current being formed from current-flow packets whose length is shorter than the cycle duration of the output signal of the body-function sensor. In this apparatus, the parameter of a periodic body function, e.g. pulse rate or blood pressure, can be influenced by the therapeutic current, wherein extent and kind of the parameter influence can be selected by setting the time interval with respect to a point of time of triggering, e.g. the R wave in the cardiac-action potential.

Here, it is furthermore advantageously provided that the electronic switching circuits include a correction stage that forms a correction signal from the frequency value or the curve shape or the amplitude value of the output signal of the body-function sensor, said correction signal being connected to a time-delay-influencing input of the time-delay stage. Thus, the change in the parameters resulting from the stimulation will be detected by the correction stage, and the correction signal emitted by the correction stage will be influenced in a manner the actual-value signal of a controlled system influences the extent of the time delay of the time-delay stage to achieve the desired extent of the change in the parameter of the respective body function in question. The desired change in the parameters of a periodic body function shall as a rule be slow, and to this end, a slow change in the settings of the above-mentioned time interval is necessary. This can be done individually by manual actuation of corresponding setting elements.

An advantageous further development of the apparatus provides that a displacement-signal generator is connected to the time-delay stage, the displacement-signal generator providing the time-delay stage with a shift signal thanks to which the delay time is adjustable in a manner slow compared to the repetition rate of the output signal of the body-function sensor. This allows for changes in the above-mentioned parameters to be simply extended to occur over longer periods of time, e.g. hours or days, without having to change any settings or the like in the meantime so as to enable a lifestyle largely unaffected by the therapy.

For attaching the at least one stimulating electrode of the apparatus to a nerve ending located in the region of the external ear, it is advantageous to configure the flexible line extending to the electrode to be as mechanically resilient as possible, and to be as short as possible so that the line is less likely to suffer from any mechanical failures during therapy. A simple implementation consists in providing for a mechanically stable line that extends from the support as far as to near the ear, from where a short, particularly flexible line extends to the respective electrode.

A preferred embodiment is characterized in that the apparatus comprises at least one electrode to be positioned at a nerve ending located in the region of the external ear, with a flexible line of said electrode extending from an insert member suitably insertable into the external auditory canal, said insert member itself being electrically connected to elements of the apparatus provided on the support. In this context, a mechanically stable flexible line can extend from the support to the insert member, and a particularly resilient, flexible line can be provided to extend from said insert member to the respective electrode, with the insert member forming a support.

A further development of the embodiment including the above insert member, it can be advantageously provided for the insert member to be configured as a housing in which at least that element of the electronic circuit of the therapeutic-current generator which delivers the therapeutic current to the electrode is provided.

A further configuration of this further development is characterized in that at least one therapeutic-current parameter, e.g. the current-flow-break program or frequency, amplitude and curve shape of the therapeutic-current-forming element of the electronic circuit of the therapeutic-current generator, is arranged in the support and controls the element of the electronic circuit of the therapeutic-current generator provided in the insert member via an electrical connection.

On the one hand, this allows for good accessibility to the elements of the support-borne electronic circuit that determine the therapeutic-current parameters for setting and monitoring purposes, and on the other hand, this provides for a small, little-visible and well-fitting configuration of the elements of the apparatus to be located in the region of the ears. The electrical connection from the support to the insert member can be a flexible line, or a wireless electrical connection can be arranged in the form of a transmitter-receiver track, and a battery can be provided in the insert member for feeding the element of the electronic circuit located in said insert member.

A variant of the apparatus provided with an insert member is characterized in that the apparatus comprises at least one electrode to be positioned at a nerve ending located in the region of the external ear, with the flexible line of said electrode extending from a housing to be worn on the outside of the ear, with at least that element of the electronic circuit of the therapeutic-current generator which delivers the therapeutic current to the electrode being arranged within said housing, and in that at least one therapeutic-current parameter, e.g. the current-flow-break program or frequency, amplitude and curve shape of the therapeutic-current-forming element of the electronic circuit of the therapeutic-current generator, is arranged in the support and controls the element of the electronic circuit of the therapeutic-current generator provided in the housing to be worn on the outside of the ear via an electrical connection. Also here, the electrical connection between the support and the housing to be worn on the outside of the ear can be a flexible line or a wireless connection in the form of a transmitter-receiver track, wherein a battery is provided in the housing to be worn on the outside of the ear for feeding the element of the electronic circuit located in said housing.

According to a further aspect, the invention is also directed at specific configurations of the virtually non-invasive punctual stimulation of nerve endings located in the region of the ears, as mentioned above, wherein in addition to considering the field of pain treatment, particular attention is also paid to the regulation of heartbeat rate and blood pressure, and to a functional neurostimulation.

In this context, a method of regulating standard-deviating values of heartbeat rate and/or blood pressure is provided which is characterized in that ear-region-located endings of neurons of tractus solitarius are stimulated by groups of successive electrical pulses generated by a therapeutic-current generator that is adjustable with respect to the starting time of the pulse groups, and that said stimulation is effected in cycle with the heartbeat cycle, and that an electrocardiogram signal is formed for this purpose by means of a sensor for electrical cardiac-action potentials provided on the patient's body, said electrocardiogram signal being supplied to a trigger circuit which reacts to the occurrence of a predefined value in the electrocardiogram signal, and which triggers an adjustable time-delay stage provided in the therapeutic-current generator, said time-delay stage starting to deliver a pulse group after the respectively adjusted delay time, wherein the starting time of the individual pulse groups is provided in the systolic region of the heartbeat cycle by adjusting the delay time, with the starting point being temporally displaced with respect to the R wave of the electrocardiogram signal, and that first a base value of the delay time is adjusted at the beginning of a regulation treatment, and that the delay time will thereafter be slowly changed for bringing the values to be regulated closer to standard values. Here, appropriate adjustment of the delay time allows for a phase displacement of the heartbeat cycle with respect to the pulse-group sequence delivered by the therapeutic-current generator, enabling a change in the heartbeat rate that corresponds to the desired regulation. A blood-pressure regulation can also be achieved by such adjustment of the pulse-group sequence delivered by the therapeutic-current generator. The slow change in the delay time results in that the heartbeat-rate and/or the blood-pressure values are gradually brought closer to the desired values, wherein the achieved heartbeat-rate and/or blood-pressure values will remain for longer periods of time even after such treatment if the change is effected at a sufficiently low speed and if a stimulation is done that lasts for hours or days.

Advantageously, the delay time is slowly changed taking into account the stimulation-produced changes in the values to be regulated. The mentioned change in the delay time can be controlled individually, e.g. by a therapist, by using appropriate setting means. Regarding the positive influence of long-term stimulation, a configuration of the method is advantageous which is characterized in that the delay time is slowly changed using an independently operating, electronic displacement stage.

Advantageously, a delay time of between 150 ms and 350 ms is set as a delay-time base value exhibited by the delivery of the stimulating pulse group with respect to the R wave of the electrocardiogram signal.

Advantageously, it is provided that the pulse groups consist of pulse sequences which are of alternatingly different polarity with respect to a base electrode, and which succeed each other at a frequency of from 70 to 110 Hz. Here, it is beneficial if the individual pulse groups include 4 to 10 pulses each. Advantageously, the individual pulses have a length of between 0.5 and 2 ms. Advantageously, the stimulation is effected with a sequence of time intervals which last from 15 min to several hours each and alternate with breaks of almost the same duration. Here, to achieve an effect that remains also after treatment, it is beneficial if at the beginning of the individual time intervals during which a stimulation is effected, the base value of the delay time is adapted to the delay time adjusted at the end of the previous time interval. Advantageously, it is furthermore provided that in the region of either ear, the stimulation is done simultaneously in a manner transcutaneous and synchronous to one another.

Furthermore, the invention provides for a method of functional neurostimulation. Here, nerve endings located in the region of the ears are transcutaneously stimulated by low-frequency currents that consist of pulse groups succeeding each other at time intervals. The individual pulse groups each consist of a pulse row, wherein the pulses succeed each other at a frequency of between 10 and 200 Hz, wherein the duration of the individual pulse groups lies between about 50 ms and 2 s. The time interval between the pulse groups expediently ranges between 200 ms and 20 s. Within these default values, the duration of the individual pulses can likewise be selected, with times between 0.5 ms and 2 ms being appropriate for many applications. Stimulations can be effected at the nerve endings located in the region of either or one ear. The pulses can have the same polarity or alternatingly different polarities.

To influence pain, sensoric A delta nerve fibers and sensoric C nerve fibers were stimulated, wherein pulse groups were used for stimulation, each consisting of 100 individual pulses succeeding each other at a frequency of 100 Hz, and the individual pulse groups had a time interval of 10 s. This stimulation was done for 15 min; 90 pulse groups. An analgesia was achieved that lasted for about 2 hours.

Further stimulations using therapeutic currents were done which consisted of pulse groups of three successive pulses each. The three pulses of each pulse group succeeded each other at a frequency of 50 Hz so that the duration of the individual pulse groups was 60 ms. The time interval between the pulse groups was 200 ms. A 15-min stimulation resulted in a suppression of the motoric function of the cerebral cortex that lasted for about 1 hour. A variant of this stimulation with pulse groups of three pulses was also done, wherein a 10-s break followed upon each 10 pulse groups, and this sequence continued over a longer period of time, wherein the motoric function of the cerebral cortex was suppressed during this time. Thus, an advantageous, functional influence on several region of the brain is possible in a non-invasive or minimum-invasive (transcutaneous) fashion, allowing for a positive influence on neurological diseases, e.g. epilepsy, Alzheimer's Disease or Parkinson's Disease.

An embodiment of the method of functional neurostimulation is characterized in that electrical-pulse stimulation of ear-region-located endings of neurons of tractus solitarius is effected during systole of each heartbeat cycle, and electrical-pulse stimulation of ear-region-located endings of neurons of lucus LC is effected during diastole of each heartbeat cycle, said electrical pulses being formed by a therapeutic-current generator, wherein an electrocardiogram signal is generated by a sensor that responds to the electrical cardiac-action potentials for synchronizing the stimulating pulses with the heartbeat cycle, said electrocardiogram signal being supplied to a trigger circuit which responds to the occurrence of a predefined value in the electrocardiogram signal, and which triggers time-delay stages provided in the therapeutic-current generator that start delivering stimulating pulses after delay times during systole and diastole.

In the last-mentioned embodiment of the method, it is advantageously provided that the stimulation is done at the neurons of tractus solitarius on one ear of a patient, and at the neurons of lucus LC on the other ear of the patient. This allows for intensification of the effect.

The invention will be explained in more detail by way of exemplary embodiments and with reference to the drawing in which such exemplary embodiments are schematically illustrated.

Therein,

FIG. 1 schematically shows a first exemplary embodiment of an inventively configured apparatus;

FIG. 2 shows the support of said apparatus in a section along line II-II of FIG. 1;

Figure 5:
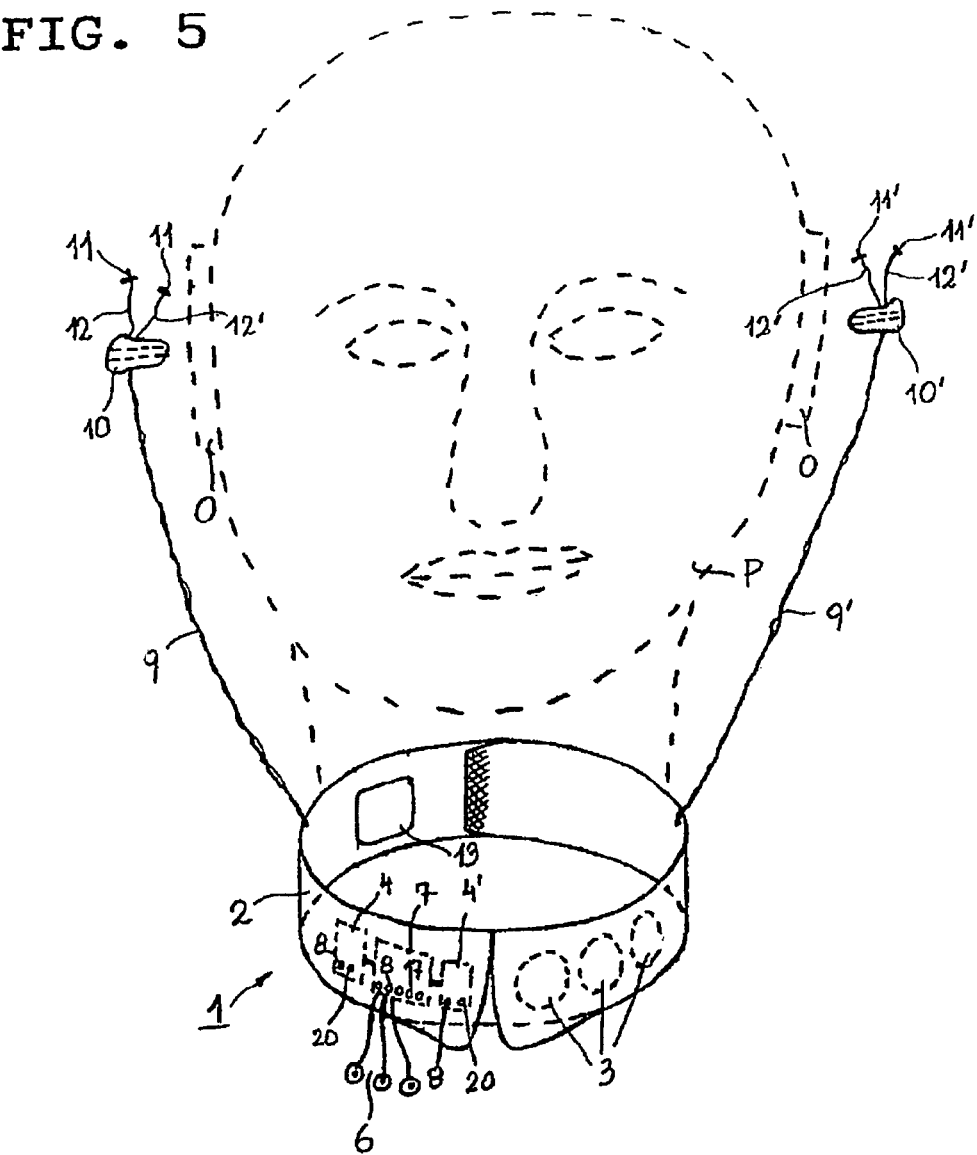
Figure 6:
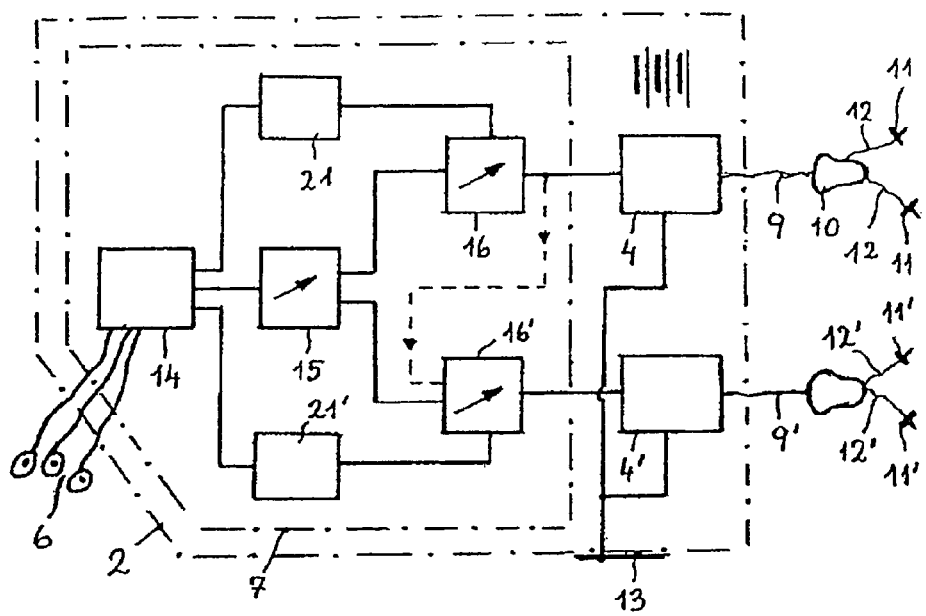
Figure 7:
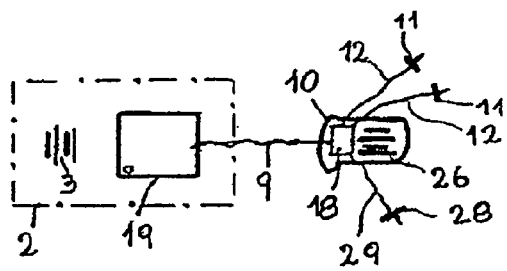
Figure 9:
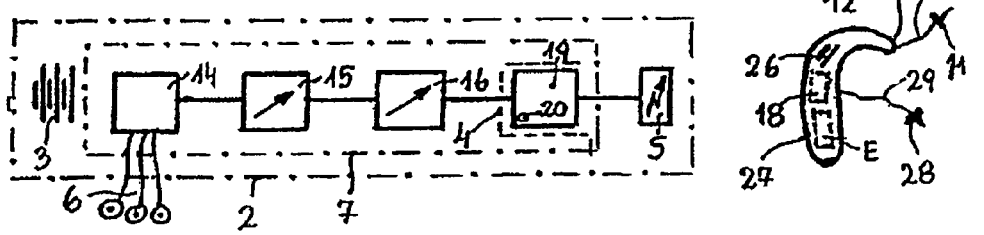
Figure 8:
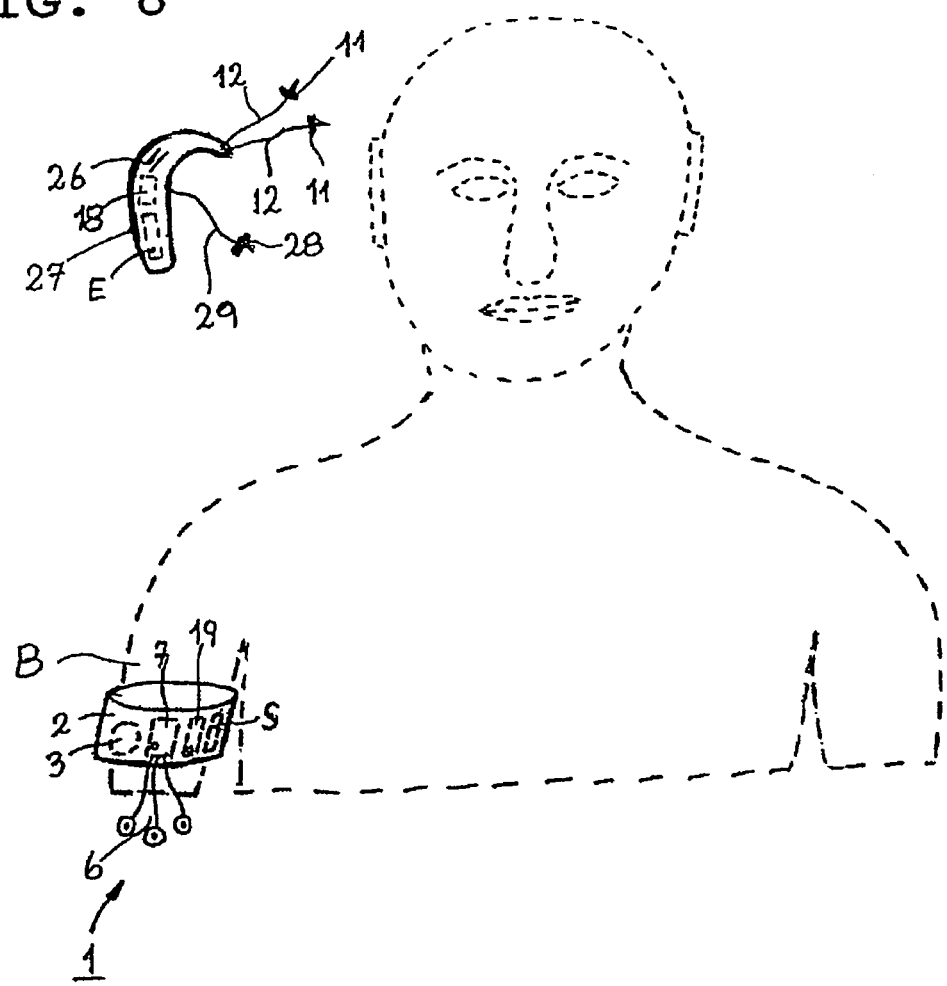

FIG. 5 schematically shows another embodiment of an inventively configured apparatus;

FIG. 6 shows a block diagram of said exemplary embodiment;

FIG. 7 shows a block diagram of another embodiment of an inventively configured apparatus;

FIG. 8 shows an embodiment of an inventively configured apparatus, wherein the support is to be arranged on a patient's upper arm, and wherein no line connection is necessary from the support to the stimulation electrodes to be positioned in a patient's region of the ears; and FIG. 9 shows a block diagram of the apparatus illustrated in FIG. 8.

FIG. 1 schematically shows an embodiment of an inventively configured apparatus 1 that comprises a support 2 to be positioned in the region of the neck A of a patient P whose head-neck region is illustrated by a dotted line in FIG. 1. The apparatus 1 is arranged for punctually stimulating nerve endings located in the region of the ears O, said nerve endings extending to the brain stem nuclei, and the apparatus 1 has a battery-fed therapeutic-current generator that feeds a low-frequency therapeutic current to small electrodes 11 to be positioned at said nerve endings. The therapeutic-current generator 4 is connected to electronic switching circuits 7 and can be formed integrated therewith or consist of several interconnected structural components, and the therapeutic-current generator 4 and the electronic switching circuits 7 are located in the support 2, the latter being configured as a collar to be laid around the neck A of the patient P. A mechanically stable, flexible line 9 extends from the one therapeutic-current generator 4 to an insert member 10 that is insertable into an ear of the patient, with particularly resilient, flexible lines 12 extending from said insert member 10 to the electrodes 11. The electrodes 11 are configured in the form of short needles provided to transcutaneously contact the nerve endings located closely under the skin in the region of the ears. The insert member 10 is pierced to not deteriorate auditory perception. The insert member may also be omitted, wherein the particularly resilient, flexible lines 12 are connected directly to the end of the stable flexible line 9. The support 2 is provided with a base electrode 13 that is contacted with the surface of the patient's skin when it is being laid around the collar-type support, wherein closing of the collar, e.g. by a hook-and-loop fastener 2a, allows for the base electrode 13 to lie closely against the surface of the patient's skin. The therapeutic-current circuit is closed via the base electrode 13, the former running through the electrodes 11 and at least one nerve ending located in the region of the patient's ears. The support 2 furthermore accommodates feed batteries 3 that deliver the operating power for the apparatus 1.

The therapeutic current fed to nerve endings via the electrodes 11 consists of a low-frequency sequence of pulses, with the nerve endings lying closely under the skin in the region of the ears of the patient to be treated, so as to effect a stimulation via said nerve endings. This pulse sequence is coordinated with a periodic body function of the patient, in the present case with the heartbeat function. To this end, a sensor 6 for electrical cardiac-action potentials is provided in the present case which is comprised of several electrodes and which is connected to a sensor amplifier 14, as illustrated in the schematic block diagram of FIG. 3. The signal amplified therein reaches an adjustable trigger 15 that delivers a control pulse to a time-delay stage 16 when a certain voltage value occurs in the repeating cycle of the cardiac-action potential, with the time-delay stage 16 being arranged downstream of the trigger 15 and controlling the therapeutic-current generator 4 with an appropriate time delay after a trigger pulse has occurred. In the therapeutic-current generator 4 an electronic circuit 5 is provided which includes a microprocessor and in whose first element 19 the therapeutic current is specified with respect to wave shape and amplitude as well as duration of pulses and pulse breaks therebetween, and duration of individual pulse sequences and breaks therebetween during which no therapeutic current flows, with said therapeutic current being formed by successive pulses and fed to the above-mentioned nerve endings. The element 19 of the electronic circuit 5 controls an output stage 18 of the therapeutic-current generator in which a current-constancy circuit arrangement 18a is provided, the latter stabilizing the therapeutic current against possibly unintended resistor changes in the electrode-patient electrical circuit.

Figure 3:
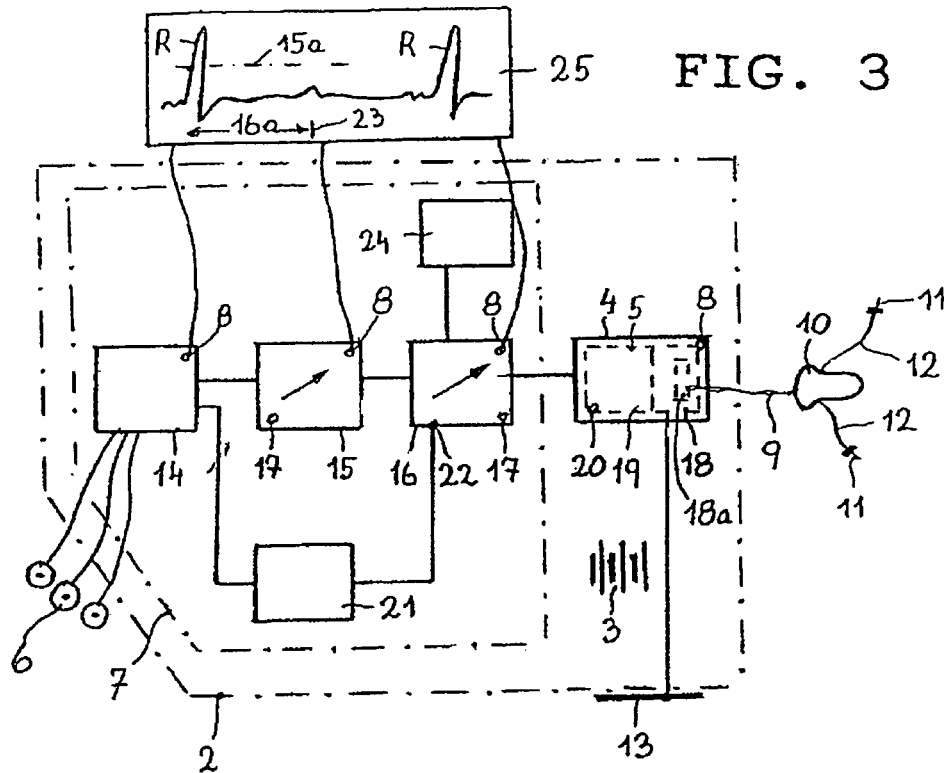
FIG. 3 shows a block diagram of the electrical structural components of said apparatus.

Connection points 8 are provided at the individual functional stages in the electronic switching circuits 7, i.e. at the sensor amplifier 14, the trigger 15, the time-delay stage 16 and the therapeutic-current generator 4, with a display 25 being connectable to said connection points 8 for illustrating the course of the potentials occurring in said functional stages. Here, as indicated in FIG. 3, the course of the cardiac-action potentials detected by the sensor 6 can be collected at the sensor-amplifier-borne connection point 8, and that point in the course of the cardiac-action potential at that a trigger pulse is delivered to the time-delay stage 16 can be made visible by displaying the respectively set value of the trigger-switching threshold 15a. Furthermore, the time interval 16a can then be displayed on the display 25, said time interval lying between the response of the trigger 15 and the delivering of a control signal 23 to the therapeutic-current generator 4, so that the point of time of the cardiac-action cycle at which there is a stimulation at the nerve endings located in the region of the ears can be seen on the display 25. For setting the point of time of triggering, it is advantageous to select the R wave occurring in the course of the cardiac-action potential, as indicated in FIG. 3.

The stimulation in question allows for the course of the body function detected by the sensor 6 to be influenced, wherein the temporal position of the stimulation in the cycle of the potential course detected by the sensor 6 is of importance. This temporal position results from the extent of time delay in the time-delay stage 16, and can be varied since the time-delay stage 16 is configured to be adjustable. As different patients respond differently to such stimulation it is advantageous to account for the response behavior of the individual patient when adjusting the time-delay stage 16, and to this end, a correction stage 21 is provided which forms a correction signal from the respective actual value, e.g. the heartbeat rate, present in the cardiac-action potential, and this correction signal will be delivered to an input 22 arranged at the time-delay stage 16, with the extent of the time delay effected in the time-delay stage 16 being changeable via said input.

As mentioned above, the individual functional stages of the electronic switching circuits 7, i.e. the trigger and the time-delay stage as well as the therapeutic-current generator 4, are adjustable and programmable as regards their functional properties, and to this end, the mentioned functional stages are connection points 17 for delivering a setting signal, and a connection point 20 for delivering a programming signal to the therapeutic-current generator 4. Such connection points, as are the connection points 8, can be implemented as simple plug contacts or as devices with transmitting-receiving technologies that may consist of inductive coupling members or be constructed by bluetooth technologies, e.g.

To provide for the possibility of gradually changing the time interval 16a which lies between the point of time of triggering and the activation of the therapeutic-current generator during a stimulation treatment that takes longer periods of time, a displacement-signal generator 24 can advantageously be provided that delivers a signal to the time-delay stage 16, the former slowly changing the extent of the time delay.

In the above description of the switching arrangement illustrated in FIG. 3, the use of a sensor 6 is mentioned that receives electrical cardiac-action potentials. Such device may also include other sensors that detect changeable body functions of patients, e.g. pulse sensors or brain-wave-detecting sensors. Blood-pressure sensors may also be additionally provided.

Figure 4:
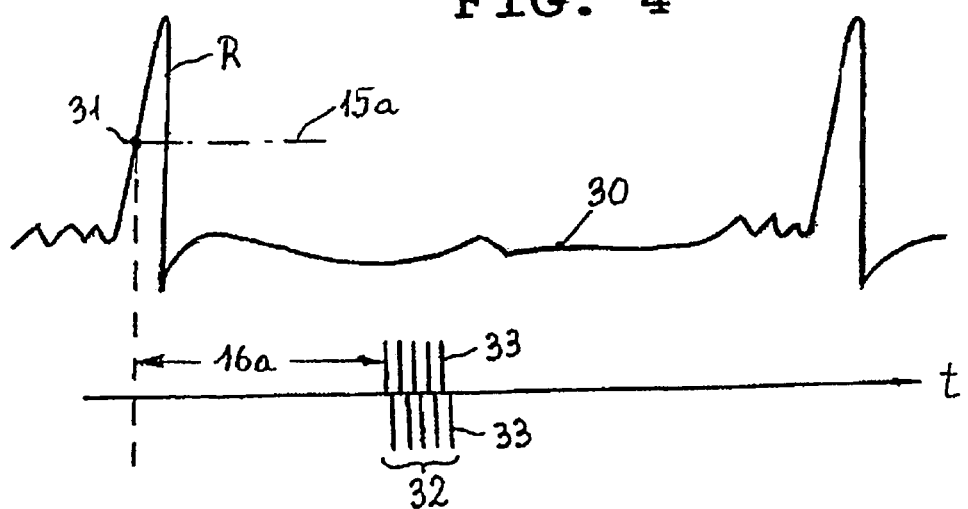
FIG. 4 shows functional diagrams as they occur in the individual stages of the block diagram of FIG. 3.

FIG. 4 is a time diagram that illustrates the temporal relations of an advantageous embodiment of the stimulation between the course of the electrical cardiac-action potential to be used as a reference value, and the therapeutic current, wherein the upper line of FIG. 4 schematically shows the course of the cardiac-action potential and the bottom line the course of the therapeutic current. On the curve that represents the cardiac-action potential 30, the point of time of triggering resulting from the trigger-switching threshold 15a is denoted by 31, and lies in the slope of the R wave. The therapeutic-current generator is activated with a delay time 16a of from 150 to 350 ms with respect to the point of time of triggering 31, and delivers one pulse group 32 per cardiac-action cycle to the stimulation electrodes positioned in the region of the ears. These pulse groups 32 consist of 4 to 10 pulses 33 each which are of alternatingly different polarity with respect to a base electrode, and which succeed each other at a frequency of from 70 to 110 Hz. Here, the individual pulses 33 have a length of between 0.5 and 2 ms.

As can be seen in FIGS. 1 and 2, the support 2 has a flexible, collar-type cover 2b on its exterior, wherein said cover 2b can be fold up in a simple manner, thus providing unhindered access to the connections 8, 17, 20 for controlling, setting and programming purposes, and allowing for the feed batteries 3 to be exchanged easily if need be. The cover 2b can also have a modern design if desired.

For different fields of application of the stimulation treatment in question, it is useful to effect a stimulation at the nerve endings located in the region of the patient's either ear. Depending on the field of application, it may comprise a simultaneous delivery of low-frequency pulse-like stimulation flows to the nerve endings located in the region of either ear, or a stimulation in which the pulse-like stimulation flows delivered to nerve endings located in the region of the patient's ear are timely shifted with respect to pulse-like stimulation flows delivered to nerve endings located in the region of the patient's other ear. The embodiment of an inventively configured apparatus illustrated in FIGS. 5 and 6 is provided to implement such possibilities of therapy. Similar to the apparatus illustrated in FIGS. 1 to 4 said apparatus 1 comprises a support 2 which is configured in the form of a collar, and at which electronic switching circuits 7, therapeutic-current generators 4, 4' and a base electrode 13 are arranged, and which accommodates feeding batteries 3 for operating the apparatus. The electronic switching circuits 7 include a sensor amplifier 14 to which a body-function sensor 6 provided with several electrodes is connected, and a trigger 15 with two outputs, wherein a first time-delay stage 16 is connected to the one output, with a therapeutic-current generator 4 being provided downstream thereof, and wherein a second time-delay stage 16' is connected to the other output, with a therapeutic-current generator 4' being located downstream thereof. Mechanically stable, flexible lines 9, 9' extend from the output stages of the therapeutic-current generators 4, 4' to insert members 10, 10' insertable into the external auditory channel of a patient's ear. Particularly resilient, flexible lines 12, 12' extend from the insert members 10, 10' to the electrodes 11, 11' which serve for contacting the nerve endings to be stimulated. The delay times of the time-delay stages 16, 16' are adjustable in a manner independent of one another, and both the electrodes 11 and the electrodes 11' can thus be supplied either with therapeutic currents temporally simultaneous to one another, or with therapeutic currents temporally displaced with respect to one another. With a modification of a temporally simultaneous activation of the time-delay stages 16, 16' by the trigger 15, it is likewise possible to connect only one time-delay stage 16 to the trigger 15, and to activate the other time-delay stage 16' via the output of the time-delay stage 16, as illustrated in FIG. 6 by dotted lines. Analogous to the embodiment of FIGS. 1 to 4, the embodiment of FIGS. 5 and 6 can also be provided with correction stages 21, 21' by means of which it is possible to influence the extend of the time delay in the time-delay stages 16, 16'.

Instead of fixing the transition from the flexible lines 9 to the flexible lines 12 mechanically by means of an insert member 10 that is secured mechanically by being inserted into the external auditory channel, it is also possible to achieve such or similar fixation with other solutions. For example, arc-type ear hooks which are to be placed around the ears, and which can be configured, e.g., as separate bodies or which can be realized by an appropriate bend of the ends of the flexible lines 9 located in the region of the ears. In the embodiment of FIGS. 1 and 4 as well as in the embodiment of FIGS. 5 and 6, there is the possibility of providing base electrodes to be arranged in the vicinity of the stimulation electrode 11 instead of the support-borne base electrode 13, wherein needle electrodes 11 to be transcutaneously inserted into regions closely under the skin are particularly considered.

FIG. 7 shows a block diagram of a simplified embodiment of an inventively configured apparatus, wherein a feed battery 3 and an electronic circuit are arranged in a support 2 which is to be positioned, e.g. in the region of a patient's neck, said feed battery 3 and electronic circuit including an element 19 of the therapeutic-current generator which is programmable as regards wave-form amplitude and time factors for the therapeutic current, and which is connected with an insert member 10 via an electrical connection in the form of a flexible line 9, with the insert member 10 being configured in the form of a housing and including the output stage 18 of the therapeutic-current generator as well as a battery 26 for feeding thereof. Flexible lines 12 extend from the insert member 10 to stimulation electrodes 11, and at least one further base electrode 28 is provided that extends from the insert member 10 along with a flexible line 29, and that is preferably configured in the form of a needle electrode.

In the embodiment of an inventively configured apparatus 1 illustrated in FIGS. 8 and 9, a support 2 is provided in the form of a tape or collar and can be worn on a patient's upper arm B. The support 2 accommodates a feed battery 3, and carries electronic switching circuits 7 and include a sensor amplifier 14, a trigger 15, a time-delay stage 16, and an element 19 of the therapeutic-current generator 4, the latter being programmable with respect to wave form, amplitude and time factors of the pulse-like therapeutic current. A body-function sensor 6 which may be a pulse sensor or a sensor for electrical cardiac-action potentials is connected to the sensor amplifier 14. As mentioned above, the trigger 15 and the time-delay stage 16 are configured to be adjustable. The output stage 18 of the therapeutic-current generator is accommodated in an arc-shaped housing 27 that likewise includes a feed battery 26 for said output stage, and stimulation electrodes 11 are connected to said output stage via flexible lines 12, and at least one base electrode 28 is connected to said output stage via a flexible line 29. The arc-shaped housing 27 can advantageously be designed in the form of a conventional phone headset. A transmitter-receiver track S, E, preferably configured by bluetooth technology, is provided to electrically connect the element of the therapeutic-current generator arranged in the support 2 to the output stage 18 of said generator in the housing 27.

Also in the embodiment illustrated in FIG. 7, the electrical connection between the electronic circuit 19 arranged in the support 2 and the output stage 18 of the therapeutic-current generator located in an insert member 10 can optionally be configured in the form of such a transmitter-receiver track if desired.

The invention claimed is:

1. A method of regulating standard-deviating values of heartbeat rate and/or blood pressure, wherein ear-region-located endings of neurons of tractus solitarius are stimulated by groups of successive electrical pulses generated by a therapeutic-current generator that is adjustable with respect to the point of time of starting the pulse groups, and wherein said stimulation is effected in cycle with the heartbeat cycle, and wherein an electrocardiogram signal is formed for this purpose by means of a sensor for electrical cardiac-action potentials provided on the patient's body, said electrocardiogram signal being supplied to a trigger circuit which responds to the occurrence of a predefined value in the electrocardiogram signal, and which triggers an adjustable time-delay stage provided in the therapeutic-current generator, said time delay stage starting to deliver a pulse group after a respectively set delay time, wherein the point of time of starting the individual pulse groups is provided in the systolic region of the heartbeat cycle by adjusting the delay time, with the point of time of starting being temporally displaced with respect to the R wave of the electrocardiogram signal, and wherein first a base value of the delay time is set at the beginning of a regulation treatment, and wherein the delay time will thereafter be slowly changed for bringing the values to be regulated closer to standard values, wherein the delay time is slowly changed taking into account the stimulation-produced changes in the values to be regulated.

2. The method according to claim 1, wherein the delay time is slowly changed using an independently operating, electronic displacement stage.

3. The method according to claim 1, wherein a delay time of between 150 and 350 ms is set as a base value.

4. The method according to claim 3, wherein the pulse groups consist of pulse sequences which are of alternatingly different polarity with respect to a base electrode, and which succeed each other at a frequency of from 70 to 110 Hz.

5. The method according to claim 4, wherein the individual pulse groups include 4 to 10 pulses each.

6. The method according to claim 4, wherein the individual pulses have a length of between 0.5 and 2 ms.

7. The method according to claim 1, wherein the stimulation is effected with a sequence of time intervals which last from 15 minutes to several hours each and alternate with breaks of almost the same duration.

8. The method according to claim 7, wherein at the beginning of the individual time intervals during which a stimulation is effected, the base value of the delay time is adapted to the delay time set at the end of the previous time interval.

9. The method according to claim 1, wherein in the region of either ear, the stimulation is done simultaneously in manner transcutaneous and synchronous to one another.

* * * * *